United States Patent
McCullen et al.

(10) Patent No.: US 11,033,655 B1
(45) Date of Patent: Jun. 15, 2021

(54) ADHESIVE COMPOSITION FOR WOUND CLOSURE

(71) Applicant: Bergen Medical Products, Inc., Cedar Knolls, NJ (US)

(72) Inventors: Seth McCullen, Greenville, SC (US); David Ingram, Anderson, SC (US); Michael Aaron Vaughn, Anderson, SC (US); William Thomas Stephens, Jr., Holly Springs, NC (US); Melissa Vinci-Rainis, Mendham, NJ (US); Robert Laudadio, Hillsdale, NJ (US)

(73) Assignee: STRATEGIC MEDICAL SOLUTIONS, LLC., Philadelphia, PA (US)

(*) Notice: Subject to any disclaimer, the term of this patent is extended or adjusted under 35 U.S.C. 154(b) by 938 days.

(21) Appl. No.: 14/964,437

(22) Filed: Dec. 9, 2015

Related U.S. Application Data

(60) Provisional application No. 62/091,016, filed on Dec. 12, 2014.

(51) Int. Cl.
*A61L 26/00* (2006.01)
*A61B 17/00* (2006.01)

(52) U.S. Cl.
CPC .... *A61L 26/0019* (2013.01); *A61B 17/00491* (2013.01); *A61L 26/00* (2013.01); *A61L 26/0004* (2013.01); *A61L 26/0061* (2013.01)

(58) Field of Classification Search
CPC .. A61L 26/0019; A61L 26/00; A61L 26/0004; A61L 26/0061; A61B 17/00491
See application file for complete search history.

(56) References Cited

U.S. PATENT DOCUMENTS

| | | | |
|---|---|---|---|
| 3,527,841 A | 9/1970 | Mcintire | |
| 3,559,652 A | 2/1971 | Banitt | |
| 3,667,472 A | 6/1972 | Halpern | |
| 3,759,264 A | 9/1973 | Coover | |
| 3,940,362 A | 2/1976 | Overhults | |
| 3,995,641 A | 12/1976 | Kronenthal | |
| 5,328,687 A | 7/1994 | Leung | |
| 5,665,817 A * | 9/1997 | Greff | C08F 22/32 524/295 |
| 5,981,621 A * | 11/1999 | Clark | A61L 24/0021 424/423 |
| 6,010,714 A * | 1/2000 | Leung | A61L 24/0042 424/448 |
| 6,743,858 B2 | 6/2004 | Hickey | |
| 8,153,743 B2 | 4/2012 | Badejo | |
| 8,198,344 B2 | 6/2012 | Zhang | |
| 8,287,901 B2 * | 10/2012 | Zhang | A61K 31/4166 424/448 |
| 2002/0095158 A1* | 7/2002 | Dixon | A61L 24/06 606/76 |
| 2011/0104508 A1* | 5/2011 | Wang | C08F 4/52 428/522 |

* cited by examiner

*Primary Examiner* — Michael B. Pallay
(74) *Attorney, Agent, or Firm* — Gearhart Law LLC

(57) ABSTRACT

Stabilized monomer and polymer adhesive compositions useful in the formulation of biomedical adhesives and sealants for application to living tissue are provided.

21 Claims, No Drawings

ADHESIVE COMPOSITION FOR WOUND CLOSURE

CROSS-REFERENCE TO RELATED APPLICATION

This application claims priority of U.S. Provisional Application Ser. No. 62/091,016, entitled "Adhesive Composition for Wound Closure", filed Dec. 12, 2014, the disclosure of which is incorporated herein by reference in its entirety.

FIELD OF THE INVENTION

The invention relates to stabilized monomer and polymer adhesive compositions useful in the formulation of biomedical adhesives and sealants for application to living tissue. More particularly, the present invention relates to stabilized formulations, and adhesive compositions for use in medical, surgical, veterinary, or other internal and external applications where adhesive may be desirable for use with living tissue.

BACKGROUND

Products in primary use for wound closure are typically surgical sutures and staples. Sutures are recognized to provide adequate wound support. However, sutures cause additional trauma to the wound site because a needle and suture must pass through tissue and the need to anesthetize the wound area via needle application. Sutures and are time-consuming to place and can cause unattractive wound closure marks.

Surgical staples have been developed to speed wound closure and provide improved cosmetic results. However, surgical staples also impose additional wound trauma and require the use of devices for positioning and applying the staples. Both sutures and staples are especially problematic in pediatric cases where the patient may have a strong fear response and refuse to cooperate with their placement and in geriatric cases where the skin tissue is weaker and prone to tearing.

Monomer and polymer adhesives or sealants are used in industrial, household, and medical or surgical applications. Included among these adhesives are cyanoacrylate monomers and polymers resulting therefrom. Since the discovery of the adhesive and sealant properties of such monomers and polymers, they have found wide use due to the speed with which they cure, the strength of the resulting bond formed, and their relative ease of use.

Medical and surgical applications of cyanoacrylate compositions include their use as alternates or aides to surgical sutures, meshes, or staples and other medical devices in wound closure, as well as for covering and protecting surface wounds of many types.

Known adhesives have been used as wound closure devices. One group of such adhesives is the monomeric forms of alpha-cyanoacrylates. Reference is made, for example, to U.S. Pat. No. 5,328,687 to Leung et al; and U.S. Pat. No. 3,527,841 to Wicker et al.; U.S. Pat. No. 3,995,641 to Kronenthal et al.; and U.S. Pat. No. 3,940,362 to Overhults, which disclose alpha-cyanoacrylates that are useful as surgical adhesives. These references are hereby incorporated by reference herein.

One topical tissue adhesive from B. Braun Melsungen AG of Germany is recommended for use only for closure of minor skin wounds and not for internal use. Moreover the manufacturer recommends that the adhesive be used sparingly or in thin films because thick films and can lead to necrosis of surrounding tissue due to an exothermic curing reaction. Moreover, films formed from this type of adhesive are typically brittle, and may permit rupture of wounds.

Plasticizers have been added to cyanoacrylate surgical adhesive compositions. For example, U.S. Pat. No. 3,759,264 to Coover, Jr. et al., U.S. Pat. No. 3,667,472 to Halpern, U.S. Pat. No. 3,559,652 to Banitt, disclose various plasticizers. These references are hereby incorporated by reference herein.

However, the incorporation of plasticizers in some adhesive compositions has led to decreased film strength of the polymerized material and instability in the composition (e.g. premature curing or significant increases in viscosity during storage or sterilization). Accordingly, such adhesive compositions are often utilized only within wound sites because they are prone to become weak and allowing wounds to rupture. Further, many such compositions are subject to degradation in strength and premature polymerization, rendering them ineffective or useless.

Various additives have been employed in cyanoacrylate surgical adhesives for the purposes of modifying the cure rate and shelf life of the adhesives. For example, cyanoacrylate polymerization inhibitors or stabilizers. Some adhesive compositions can contain significant amounts of impurities and, thus, require substantial amounts of stabilizer to inhibit premature polymerization of the monomer.

Certain adhesives can include both plasticizers and stabilizing agents. For example, U.S. Pat. No. 5,480,935 to Greff et al, which is hereby incorporated by reference herein, describes a tissue adhesive having a large percentage of (18-25%) plasticizer and a polymerization inhibitor. However, some of the plasticizers disclosed can be toxic and may not be suitable for use in biocompatible medical adhesives.

The present invention overcomes known problems of topical adhesives and provides stable adhesive compositions having enhanced and desirable properties for use in biomedical wound closure or sealing, such as optimized viscosity for application to wounds, stability before initiation, cure time calculated for workability, low exothermic profile for minimization of tissue damage, and superior mechanical strength and flexibility.

SUMMARY

The present invention is based on the discovery that combining certain monomers described hereinafter with a plasticizing agent and thickening agent or agents, with stabilizers and solvent or diluent provides a stabile surgical adhesive composition that, after application to wounds or incisions, polymerizes to form a strong yet flexible bond proximate to a wound or incision site with low toxicity, and low heat of reaction.

In one aspect of the present invention, a stable biocompatible adhesive composition includes a cyanoacrylate monomer capable of polymerization, a viscosity modifier, a plasticizer, a solvent, a first stabilizer, and a second stabilizer.

In one embodiment of this aspect, the cyanoacrylate monomer can be 2-octyl cyanoacrylate.

In certain embodiments, the 2-octyl cyanoacrylate can have a purity of 98% or greater.

In some embodiments, the viscosity modifier can be polymethyl methacrylate (PMMA).

In certain embodiments, the PMMA can include a first PMMA and a second PMMA. The first PMMA can have a viscosity greater that the viscosity of the second PMMA.

In some embodiments, the plasticizer can be tributyl O-acetylcitrate (TBOAC).

In other embodiments, the solvent or diluent can be acetone.

In certain embodiments, the first stabilizer can be butylated hydroxyanisole (BHA).

In some embodiments, the second stabilizer can be sulfur dioxide ($SO_2$).

In one particular embodiment, the cyanoacrylate monomer can be 2-octyl cyanoacrylate, the viscosity modifier can be polymethyl methacrylate (PMMA), the plasticizer can be tributyl O-acetylcitrate (TBOAC), the solvent can be acetone, the first stabilizer can be butylated hydroxyanisole (BHA), and the second stabilizer can be sulfur dioxide ($SO_2$).

In yet another embodiment, wherein the weight % of the 2-octyl cyanoacrylate can be between about 80% and about 90%; the weight % of the polymethyl methacrylate can be between about 3% and about 5%, preferably about 3.75%, the weight % of the tributyl O-acetylcitrate can be between about 4% and about 6%; the weight % of the acetone can be between about 4% and about 6%, the weight % of the butylated hydroxyanisole can be between about 5000 ppm and about 15000 ppm, and the weight % of the sulfur dioxide can be between about 100 ppm and about 300 ppm.

In some embodiments, the composition can include an effective amount of benzalkonium chloride (BZC) or hexamethylenetetramine (HMTA) to initiate or accelerate the polymerization of the composition. The BZC or HTMA can be dissolved in a solvent and applied to an applicator. When the composition comes in contact with the applicator, a polymerization reaction can be initiated, thereby producing a durable, flexible, biocompatible wound sealant adhesive.

In another aspect of the present invention, an adhesive composition can include from about 83 weight % to about 89 weight % 2-octyl cyanoacrylate monomer, from about 2 weight % to about 5 weight % of a first PMMA viscosity modifier, the first modifier having a viscosity of from about 400,000-500,000 Da, between from about 2 weight % to about 5% of a second PMMA viscosity modifier, said second modifier having a viscosity from about 100,000-130,000 Da, from about 3% to about 6% tributyl O-acetylcitrate, from about 3% to about 7% acetone; and from about 5000 ppm to about 15000 parts per million (ppm) butylated hydroxyanisole.

In one embodiment of this aspect, the composition can further include from about 100 ppm to about 300 ppm sulfur dioxide.

In some embodiments, the composition can further comprise a polymerization initiator and a polymerization accelerator.

In certain embodiments, wherein the initiator can be benzalkonium chloride (BZC) and the accelerator can be hexamethylenetetramine (HMTA).

In some embodiments, the benzalkonium chloride (BZC) can be from about 0.1-0.3 weight % and the hexamethylenetetramine (HMTA) can be from about 0.1-0.3 weight %.

In certain embodiments, the BZC and the HTMA can be dissolved in a solvent and applied to an applicator. When the remaining components (monomer, plasticizer, viscosity modifier, stabilizers, and the like) come in contact with the applicator, the polymerization reaction can be initiated thereby producing a durable, flexible, biocompatible wound sealant adhesive.

In another aspect of the present invention, an adhesive composition can include about 84 to about 87% by weight 2-octyl cyanoacrylate monomer, about 2% to about 5% by weight of a first PMMA, the first PMMA having a viscosity of about 400,000-500,000 Da, about 4% to about 5% of a second PMMA, the second PMMA having a viscosity of about 110,000-120,000 Da, about 4 to about 6 wt % acetyl tributyl citrate, about 3% to about 7 wt % acetone, about 0.20 to about 0.25 wt % benzalkonium chloride (BZC), and about 0.18 wt % to about 0.24 wt % hexamethylenetetramine (HMTA), wherein weight % (wt %) of the BZC and the HMTA can be defined as grams/mL when dissolved in acetone and applied to an applicator tip.

In another aspect of the present invention, a system for treating living tissue can include a first reservoir containing polymerizable 2-octyl cyanoacrylate monomer, polymethyl methacrylate, tributyl 0-acetylcitrate, acetone, butylated hydroxyanisole and sulfur dioxide.

In another aspect of the invention, an applicator can be capable of combining the contents of a first reservoir with the contents of a second reservoir thereby forming an adhesive composition that cures forming a solid film. The adhesive composition can be applied to living tissue in order to seal a wound.

In one embodiment of this aspect a polymerization initiator can be disposed in the second reservoir with the polymerization accelerator.

In some embodiments, the polymerization initiator can be benzalkonium chloride (BZC) and the polymerization accelerator can be hexamethylenetetramine (HMTA).

In another aspect of the invention, the composition can include from about 80 to 90 percent by weight of an alkyl cyanoacrylate, from about 100 to 300 parts per million of $SO_2$ as a first polymerization inhibitor, from about 10000 to 30000 parts per million of BHA as a second polymerization inhibitor, from about 4 to 6 percent by weight of a biocompatible plasticizer, from about 3 to about 5 percent by weight of a viscosity modifier, and from about 4 to 6 percent by weight of a solvent.

In yet another aspect, the composition can include from about 80 to 90 weight percent of 2-octyl cyanoacrylate, from about 100-200 parts per million of $SO_2$ as a first polymerization inhibitor, from about 10000-20000 parts per million of BHA as a second polymerization inhibitor, from about 3 to 5 weight percent of PMMA as a viscosity modifier, from about 3 to 5 weight percent of TBOAC as a plasticizer and from about 3 to 5 weight percent of acetone.

In one aspect of the present invention, the adhesive composition comprises a monomer, a plasticizer, and a thickener. The mixture can include a solvent. The mixture will polymerize when exposed to a polymerization initiator. An accelerator can be utilized to optimize the polymerization reaction.

In one embodiment of this aspect, the monomer can comprise 2-octyl cyanoacrylate (2-OCA), the plasticizer can include tributyl O-acetylcitrate (TBOAC) and the thickener can include polymethyl methacrylate (PMMA).

In a particular embodiment, the adhesive composition comprises about 80% to about 90% 2-octyl cyanoacrylate monomer, about 3% to about 10% tributyl 0-acetylcitrate and about 3% to about 10% PMMA. The solvent can be about 3-7% by weight.

In another embodiment, the adhesive composition comprises about 86% 2-octyl cyanoacrylate monomer, about 4.8% tributyl O-acetylcitrate and about 3.75% PMMA. The solvent can be about 5% by weight.

In some embodiments, the initiator can be tributylhexadecylphosphonium bromide (TBHD) and the accelerator can be hexamethylenetetramine (HMTA).

In a particular embodiment, the TBHD can be between about 0.15% and about 0.30%.

In other embodiments, the HMTA can be between about 0.15 and 0.30 wt %.

In a particular embodiment, the TBHD can be about 0.22 wt % and the HMTA about 0.21 wt %. The THBD and HTMA can be dissolved in acetone and applied to an applicator tip in about a 230 µL volume to initiate the reaction.

In certain embodiments, the PMMA viscosity can be between about 400,000 and about 500,000 Da.

In some embodiments, the solvent can be a ketone.

In particular embodiments, the solvent can be acetone.

In a particular embodiment of this aspect, the adhesive composition comprises about 86% 2-octyl cyanoacrylate monomer, about 4.8% acetyl tributyl 0-acetylcitrate, and about 4.2% PMMA. The solvent can be about 5% acetone by weight. The TBHD can be about 0.22 wt % and the HMTA can be about 0.21 wt %.

In certain embodiments, the THBD and HTMA can be dissolved in acetone and applied to an applicator tip such that when the other components come in contact with the applicator tip, the polymerization reaction is initiated or accelerated to produce a durable, flexible, biocompatible wound sealant having an optimized cure time, high strength, and minimal exothermic reaction.

In one particular embodiment, the formulation can comprise about 80 to about 83% 2-octyl cyanoacrylate monomer, about 2% to about 5% of a first PMMA. The first PMMA can be about 400,000-500,000 Da, and about 4 to about 5% of a second PMMA, the second PMMA being about 115,000 Da. The formulation can include about 4% to about 6% acetyl tributyl citrate plasticizer, about 3% to about 7% acetone solvent, about 0.20 wt % to about 0.25 wt % tributylhexadecylphosphonium bromide (TBHD) initiator, and about 0.18 wt % to about 0.24 wt % hexamethylenetetramine (HMTA) accelerator, wherein weight % can be defined as grams/mL when dissolved in acetone and applied to a tip prior to dispensing.

In another embodiment, the formulation comprises about 82.82% 2-octyl cyanoacrylate, about 2.65% PMMA having a viscosity of 400,000-500,000 Da, about 4.73% PMMA having a viscosity of about –115,000 Da, about 4.8% Acetyl tributyl citrate, about 5% Acetone, about 0.22 wt % tributylhexadecylphosphonium bromide, about 0.21 wt % hexamethylenetetramine (HMTA) wherein wt % is defined as grams/mL.

In another aspect of the present invention, stabilization sterilization may be desirable. Butylated hydroxyanisole (BHA) can be used as a free radical stabilizer. It was discovered herein that the combination of BHA stabilizer and benzalkonium chloride (BZK) initiator can be optimized for formulations requiring sterilization.

In one embodiment of this aspect, the adhesive composition comprises a monomer, a plasticizer, a first thickener, a second thickener and a stabilizer. The adhesive composition can include a solvent. The adhesive composition will polymerize when exposed to a polymerization initiator or accelerator.

In a certain embodiment of this aspect, the monomer can comprise 2-octyl cyanoacrylate (2-OCA), the plasticizer can include tributyl O-acetylcitrate and the thickener can include polymethyl methacrylates (PMMA).

In a particular embodiment, the adhesive composition comprises about 80% to about 90% 2-octyl cyanoacrylate monomer, about 3% to about 10% tributyl 0-acetylcitrate and about 3% to about 10% PMMA. The solvent can be about 5% by weight.

In another embodiment, the adhesive composition comprises about 86% 2-octyl cyanoacrylate monomer, about 4.8% acetyl tributyl citrate and about 4.2% PMMA. The solvent can be about 5% by weight.

In some embodiments of this aspect, the initiator can be benzalkonium chloride (BZC) and the stabilizer can be butylated hydroxyanisole (BHA).

In particular embodiments, the BZC can be between about 10 mg and about 30 mg and the BHA can be between about 2 wt % and about 5 wt % or about 20,000 ppm to about 50,000 ppm.

In certain embodiments the PMMA viscosity is between about 400,000 and about 500,000 Da.

In some embodiments, the solvent can be a ketone.

In particular embodiments, the solvent can be acetone.

In a particular embodiment of this aspect, the adhesive composition comprises about 86% 2-octyl cyanoacrylate monomer, about 4.8% acetyl tributyl citrate, and about 4.2% PMMA. The solvent can be about 5% acetone by weight. The BZC can be between about 10 mg and about 30 mg and the BHA can be between about 20,000 ppm and about 50,000 ppm or about 2 to about 5 wt %.

In another embodiment, the formulation can comprise about 80 to about 83% 2-octyl cyanoacrylate monomer, about 2% to about 5% PMMA. The PMMA can be about 400,000-500,000 Da, and about 4% to about 5% PMMA 115,000 Da. The formulation can include about 4% to about 6% tributyl O-acetylcitrate plasticizer, about 3% to about 7% acetone solvent, the BZC can be between about 10 mg and about 30 mg and the BHA can be between about 2 wt % and about 5 wt % or about 20,000 ppm to about 50,000 ppm.

In yet another embodiment, the adhesive composition comprises about 82.82% 2-octyl cyanoacrylate, about 2.65% PMMA having a viscosity of 400,000-500,000 Da, about 4.73% PMMA having a viscosity of about –115,000 Da, about 4.8% tributyl O-acetylcitrate, about 5% Acetone, the BZC can be between about 10 mg and about 30 mg and the BHA can be between about 2 wt % and about 5 wt % or about 20,000 ppm to about 50,000 ppm.

In one embodiment of this aspect, the BHA can be 20,000 ppm and the BZC can be about 7.5 mg.

In another embodiment of this aspect, the BHA can be 30,000 ppm and the BZC can be about 10 mg.

In yet another embodiment of this aspect, the BHA can be 50,000 ppm and the BZC can be about 15 mg.

In a particular embodiment of some aspects, the setting time of the adhesive can be about 60-120 seconds, the butt joint strength can be about 5-15 lbf, and the peak reaction temperature can be below about 40 degrees C.

In another embodiment of some aspects, the setting time of the adhesive can be about 90 seconds, the butt joint strength can be about 10 lbs., and the peak reaction temperature can be below about 32 degrees C.

In some embodiments of the invention, the BZC can be loaded onto an applicator tip in which the adhesive is expressed through and can be kept separate from the adhesive composition until use. The mass in mg of the BZC can be added in a volume of about 230 microliters of fluid to coat the tip with BZC prior to contacting.

In some embodiments, the stability is measured by an increase in viscosity over time after exposure to temperature, electron beam radiation, or both.

It will be appreciated that the amount of initiator or accelerator or both can be adjusted for any specific applicator to provide the appropriate concentration based on the surface area required for chemical initiation or acceleration.

DESCRIPTION

This invention relates to specific alkyl cyanoacrylate compositions that are particularly well suited for topical application to human skin.

As used herein, the following terms have the following meanings:

The term "cyanoacrylate" refers to an adhesive compound or mixture of compounds based on cyanoacrylate monomers. Partial polymers (i.e., oligomers) of such cyanoacrylates are also encompassed within this definition. A preferred cyanoacrylate for use in this invention is octyl-2-cyanoacrylate (2-OCA).

The term "biocompatible plasticizer" refers to any material which is soluble or dispersible in alkyl cyanoacrylate, which increases the flexibility of the resulting polymer coating on the skin surface, and which is compatible with the skin as measured by the lack of skin irritation. Specific stabilizers can include, by way of example only, tributyl O-acetylcitrate, butyl benzyl phthalate, dibutyl phthalate, diethyl phthalate, dimethyl phthalate, dioctylphthalate, n-butyryl tri-n-hexyl citrate, benzoate esters of di- and poly-hydroxy branched aliphatic compounds, tri(p-cresyl) phosphate, and the like.

The particular plasticizer employed can be critical and must not produce skin irritation as measured by well-known assays such as primary skin-irritation. The plasticizer must not cause the adhesive to be weak or polymerize prematurely. A particularly preferred plasticizer is tributyl O-acetylcitrate.

Compositions contain a sufficient amount of a viscosity modifier or combination of modifiers to provide for a viscosity of from about 20 to 500 centipoise at 20° C. The thickening agent employed is a biocompatible material which increases the viscosity of the cyanoacrylate composition and includes, by way of example, a partial polymer of the cyanoacrylate, polymethyl methacrylate (PMMA) or polymers soluble in the alkyl cyanoacrylate. Thickening agents are deemed to be biocompatible if they are both soluble in the alkyl cyanoacrylate composition and are compatible with the skin as measured by the lack of skin irritation. The lack of skin irritation can be measured by conventional procedures such as primary skin irritation. Thickening agents must not cause the adhesive to be weak or polymerize prematurely.

At the amounts employed, the stabilizer, for example, sulfur dioxide, and the plasticizer are soluble in the cyanoacrylate and, accordingly, after mixing a uniform solution is produced. The solution can be optionally filtered to remove insoluables.

Some compositions can be prepared generally mixing the requisite amounts of the liquid components until a homogeneous mixture is obtained. When utilized, SO2 gas can be bubbled through the mixture. The mixing procedure cab be conventional and is typically conducted under anhydrous conditions to ensure against water contamination of the composition.

The specific viscosity employed for the cyanoacrylate composition depends, in part, on the intended application of the composition. For example, relatively low viscosities are often preferred where application is to be made to a large surface area. This preference results from the fact that those forms are less viscous and, accordingly, will permit easy application to large surface areas of a thin application. Contrarily, where application is to be made to a specific position on the skin, higher viscosity materials are preferred to prevent "running" of the material to unintended locations.

The particular thickening agent employed to enhance the viscosity of the composition can be critical. Preferred thickening agents include polymethyl methacrylate (PMMA) monomer, oligomer, or blends thereof.

Upon contact with skin moisture and tissue protein, the alkyl cyanoacrylate will polymerize or, in the case of partially polymerized alkyl cyanoacrylate, will further polymerize, at ambient conditions (skin temperature) over about 30 seconds to 120 seconds to provide a solid layer which forms over and strongly adheres to the surface of the skin.

The compositions may additionally contain one or more optional additives such as colorants (e.g. D&C violet), perfumes, anti-diffusion agents, rubber extenders, modifying agents, etc. Optional additives should be both miscible and compatible with the cyanoacrylate adhesive. Compatible additives are those that do not prevent the use of the cyanoacrylate adhesives in the manner described herein.

In general, colorants are added so that the polymerized film will contain a discrete and discernable color. Perfumes are added to provide a pleasant smell to the formulation. Rubber extenders are added to further enhance the flexibility of the resulting polymer coating. The amount of each of these optional additives employed in the cyanoacrylate adhesive composition is an amount necessary to achieve the desired effect.

The resulting composition is generally stored in an applicator for use in a single dose application such as a sealed frangible vile or for use in repeated applications. Single dose applicators include those having a breakable or removable seal that prevents moisture, including atmospheric moisture, from contacting the formulation and potentially causing unwanted polymerization.

The viscosity of an adhesive composition must be controlled in order to prevent undue escape of the adhesive from any given area to which it is applied as well as to allow sufficient time for the monomeric material to polymerize and thus to bring about the desired bonding action, such as wound sealing or closure.

The problem been generally recognized by workers in this field and a rather wide variety of viscosity modifiers for alpha-cyanoacrylate adhesives have been suggested in patents and the literature. The present invention relates to among other aspects, a viscosity modifier system for use as a component of this type of adhesive and having solubility in alpha-cyanoacrylates and a high order of heat stability. These properties render such modifiers particularly advantageous when used as components of surgical adhesives which can be subjected to heat, filtration, or electron beam sterilization procedures in order to provide that the resulting compositions are sterile and safe for their intended uses.

Another requirement of alpha-cyanoacrylate adhesive compositions which are to be employed for surgical uses is that both the adhesive component and the viscosity modifier must be relatively non-toxic and each component must be biodegradable, that is, each must be susceptible of biochemical transformation or degradation which will result in harmless products which can be readily absorbed into and carried away from the point of application by the body fluids and thus ultimately eliminated from the system.

This invention has as an object to provide alpha-cyanoacrylate adhesive compositions having viscosity and other characteristics which render them particularly useful as wound closure adhesives or sealants.

One object is to provide alpha-cyanoacrylate adhesive compositions having viscosity and other characteristics which render them particularly useful for surgical applications.

A further object is to provide alpha-cyanoacrylate adhesive compositions particularly adapted for use in the surgical field and characterized by the fact that both the adhesive and the viscosity modifying components are biocompatible.

A further object is to provide alpha-cyanoacrylate adhesive compositions for both general and surgical uses containing a viscosity modifier which is soluble in cyanoacrylate monomers and has a high degree of stability under sterilization conditions and during storage.

Another object is to provide alpha-cyanoacrylate adhesive compositions containing a biocompatible viscosity modifier and stabilized against polymerization by the presence of one or more polymerization inhibitors.

In order to stabilize the compositions of the present invention against unwanted rapid polymerization, and also to provide a satisfactory shelf life, one or more polymerization inhibitors may be employed. The inhibiting material may be an acidic stabilizer or a free radical scavenger or both. A free radical scavenger may be defined as a material which has the ability to react with an unpaired electron to produce a substance which does not initiate further polymerization.

Among the free radical scavengers which may be employed as stabilizers in the adhesive compositions of the invention may include: hydroquinone, monomethyl ether of hydroquinone, butylated hydroxyanisole, butylated hydroxytoluene, and t-butyl hydroquinone. BHA is a preferred stabilizer.

The PMMA component(s) employed as the viscosity modifier in accordance with the invention may be one or more PMMA viscosities.

In formulating adhesive compositions in accordance with the invention, the concentration of PMMA in the monomeric alpha-cyanoacrylate may, the range of 2-6 percent by weight of the total composition. The formulations and adhesive compositions of the instant invention were studied in order to optimize various properties such as viscosity and adhesive strength. For example, different viscosity blends of PMMA monomer or oligomer may be combined or optimize the viscosity and strength characteristics of the cured and uncured compositions.

As used herein, the term ppm (parts per million) refers to the amount of stabilizer ($m_{stabilizer}$) in relation to the mass of the original adhesive composition ($m_f$) by the formula: $m_{stabilizer}/(m_{stabilizer}+m_f) \times 1{,}000{,}000$.

Numerous viscosity modifiers were screened for development of tissue adhesives. PMI and PMMA were among the thickeners evaluated in nine different adhesive compositions. Based on the test results, PMMA or blends thereof, was selected as the most desirable viscosity modifier.

Relative viscosity, butt joint strength, peel strength, tensile strength, maximum reaction temperature, setting or cure time, and enthalpy of reaction were measured to select optimum parameters for desirable embodiments of the invention.

Formulations developed herein exhibited increased strength, equivalent adhesive properties, and lower peak temperature exothermic reactions than known target materials while producing flexible compliant adhesive barriers.

Testing was performed to optimize and validate various initiator or accelerator formulations. Enhanced setting time of less than about 120 seconds and butt joint strength of about 10 lbs. were goals for some of the development tests.

Several levels of butylated hydroxyanisole (BHA) (e.g. 5,000 and 15,000 ppm) were tested for stability under simulated e-beam sterilization conditions at various radiation levels.

Additional testing was performed with BHA at 20,000, 30,000 and 50,000 ppm with various initiators to develop a stabilized adhesive composition having optimum setting time, reaction temperature, and strength. BZC was selected as a preferred initiator at levels between about 5000 and about 20000 ppm.

Adhesive composition with BHA levels of 20, 30, and 50K ppm at 10, 15, and 20 kGy radiation levels were characterized. Control adhesives formulated without stabilizer increased viscosity at all exposure levels.

Compositions having BHA levels between about 10K, 20K ppm, 30K ppm, and 50K ppm and BZC levels between about 7.5 mg, 10 mg, and 15 mg respectively were characterized.

Viscosity, setting time, reaction temperature, and butt joint strength were evaluated. Setting time of about 60-120 seconds, butt joint strength of about 10 lbs., and reaction temperature below about 32 C were achieved for some optimized adhesive compositions.

The following examples illustrates certain embodiments of the invention but is not meant to limit the scope of the claims in any way.

EXAMPLES

Example 1 summarizes a study related to one non-limiting example of an embodiment of the present invention. In the study to determine stability under exposure to electron beam radiation, the wt % of cured cyanoacrylate of several samples was measured using HNMR. The results are shown in Table I below.

TABLE I

| Sample | PMMA | TBOCA | Acetone | BHA | Total Cyanoacrylate | Cured CA |
|---|---|---|---|---|---|---|
| 30 2-Control (30° C.) Day 68 | 3.82% | 4.83% | 3.11% | 5151 ppm | 87.73% | 0% |
| 2 2-EB-5 (30° C.) Day 68 | 3.68% | 4.93% | 3.04% | 4074 ppm | 87.95% | 3.42% |
| 2-EB-5 50° C. Day 44 Sample 2 | 4.00% | 5.09% | 2.74% | 4729 ppm | 87.70% | 5.01% |
| 30 2-Control (50° C.) Day 71 | 4.11% | 5.06% | 3.08% | 4447 ppm | 87.30% | 4.99% |
| 2-EB-5 (50° C.) Day 71 | 4.09% | 5.13% | 3.04% | 4350 ppm | 87.31% | 8.41% |
| 6-EB-10 (30° C.) Day 78 | 3.50% | 5.07% | 2.72% | 8457 ppm | 87.86% | 1.32% |
| 6-EB-10 (50° C.) Day 78 | 3.27% | 5.06% | 2.59% | 7337 ppm | 88.35% | 11.44% |

For example, a formulation control composition showed 0% cured material after 68 days at 30 degrees C. Exposure to e-beam radiation increased the cured weight % at 30 and 50 degrees respectively. The composition was optimized for maximum stability under time at temperature or radiation conditions. Sample 6-EB-10 demonstrated surprising stability after exposure to 10 kGy after 78 days, that is, less than 2% cured cyanoacrylate was detected by HNMR.

Example 2

In another non limiting example, mechanical properties were studied on a formulation comprising about 3.75% PMMA and 10,000 ppm BHA.

TABLE II

| Sample | 27D | 28D | 29D |
|---|---|---|---|
| 1 | 402.79 | 536.38 | 507.44 |
| 2 | 432.88 | 634.60 | 388.77 |
| 3 | 358.67 | 442.22 | 429.29 |
| 4 | 632.67 | 497.16 | 498.98 |
| 5 | 434.45 | 630.88 | 449.95 |
| 6 | 439.25 | 588.56 | 669.64 |
| 7 | 609.58 | 504.70 | 604.02 |
| 8 | 567.72 | 584.71 | 635.87 |
| 9 | 555.05 | 535.81 | 470.97 |
| 10 | 629.50 | 559.40 | 496.91 |
| Average | 506.26 | 551.44 | 515.18 |
| StDev | 103.02 | 60.83 | 92.22 |

As shown in Table II, all values are listed in Newtons (N). Testing was performed according to ASTM F2255-05 (Re-approved 2010) Standard Test Method for Strength Properties of Tissue Adhesives in Lap-Shear by Tension Loading.

Setting time of 30-120 seconds was achieved for some compositions studied. Butt-joint strength was at or near 10 lbs. and reaction temperature was below 32° C.

This study demonstrated a variety of stable compositions with adequate workability, strength, and heat of reaction.

Example 3

In one illustrative non-limiting study, as shown in table III below, viscosity measurements were taken on various embodiments of the invention.

TABLE III

| Sample | 2E35 | 6E35 | 10E35 | 2E310 | 6E310 | 10EB10 | CONTROL |
|---|---|---|---|---|---|---|---|
| Rep 1 | 60.1 | 59.4 | 57.8 | 52.9 | 54.1 | 46.9 | 50.8 |
| Rep 2 | 54.6 | 59.5 | 60.1 | 52.0 | 52.5 | 50.8 | 50.5 |
| Rep 3 | 57.0 | 60.9 | 57.9 | 52.9 | 52.3 | 51.2 | 51.4 |
| Avg Viscosity (cP) | 57.2 | 59.9 | 58.6 | 52.6 | 53.0 | 49.6 | 50.9 |
| Std Dev. | 2.8 | 0.8 | 1.3 | 0.5 | 1.0 | 2.4 | 0.5 |

Sample compositions were stored at 30 degrees C. for 91 days. Nominal changes in viscosity and standard deviation were reported, thus demonstrating desirable shelf life and stability for at least 3 months. Samples coded EB5 and EB10 were exposed to 5 kGy and 10 kGy respectively. Control samples were not exposed to radiation.

From the foregoing description, various modifications and changes in the composition and method will occur to those skilled in the art. All such modifications coming within the scope of the appended claims.

What is claimed is:

1. A stable biocompatible adhesive composition comprising:
   a 2-octyl cyanoacrylate monomer capable of polymerization and having a purity of at least 98%, wherein a weight % of the 2-octyl cyanoacrylate monomer is between about 83% to about 89%;
   a first viscosity modifier comprising polymethyl methacrylate (PMMA), wherein the first viscosity modifier comprises a molecular weight from about 400,000 Da to about 500,000 Da;
   a second viscosity modifier comprising the PMMA, wherein the second viscosity modifier comprises the molecular weight from about 100,000 Da to about 130,000 Da, and wherein each of the first viscosity modifier and the second viscosity modifier comprises the weight % between about 2% to about 5%;
   a plasticizer comprising tributyl O-acetylcitrate (TBOAC), wherein the weight % of the TBOAC is between about 3% to about 6%;
   a solvent having the weight % between about 3% to about 7%;
   a first stabilizer in an amount of about 5,000 parts per million (ppm) to about 15,000 ppm;
   a second stabilizer in the amount of about 100 ppm to about 300 ppm;
   a polymerization initiator comprising benzalkonium chloride (BZC), wherein the weight % of the BZC is between about 0.1% to about 0.3%; and
   a polymerization accelerator comprising hexamethylenetetramine (HMTA), wherein the weight % of the HMTA is between about 0.1% to about 0.3%.

2. The composition of claim 1, wherein said 2-octyl cyanoacrylate monomer has a purity of 99% by weight or greater.

3. The composition of claim 1, wherein said solvent is acetone.

4. The composition of claim 1, wherein said first stabilizer is butylated hydroxyanisole (BHA).

5. The composition of claim 1, wherein said second stabilizer is sulfur dioxide ($SO_2$).

6. The composition of claim 1, wherein said solvent is acetone, said first stabilizer is butylated hydroxyanisole, and said second stabilizer is sulfur dioxide.

7. The composition of claim 1, wherein:
   the weight % of each of said first viscosity modifier and said second viscosity modifier is from about 3% to about 5%;
   the weight % of said TBOAC is from about 4% to about 6%; and
   the weight % of said solvent is from about 4% to about 6%.

8. The composition of claim 1,
   wherein said BZC is dissolved in another solvent and applied to an applicator, and
   wherein said other solvent substantially evaporates before said stable biocompatible adhesive composition comes into contact with said applicator, thereby initiating a polymerization reaction and producing a solid, biocompatible wound sealant.

9. An adhesive composition comprising:
   between about 83 weight % and about 89 weight % of a 2-octyl cyanoacrylate monomer having a purity of at least 98%;

between about 2 weight % and about 5 weight % of a first polymethyl methacrylate (PMMA) viscosity modifier having a molecular weight from about 400,000 Da to about 500,000 Da;

between about 2 weight % and about 5 weight % of a second PMMA viscosity modifier having the molecular weight from about 100,000 Da to 130,000 Da;

between about 3 weight % to about 6 weight % tributyl O-acetylcitrate (TBOAC);

between about 3 weight % and 7 weight % acetone;

between about 5,000 parts per million (ppm) and about 15,000 ppm of butylated hydroxyanisole;

between about 100 ppm and about 300 ppm of sulfur dioxide;

between about 0.1 weight % and 0.3 weight % of a polymerization initiator, the polymerization initiator comprising benzalkonium chloride (BZC); and between about 0.1 weight % and 0.3 weight % of a polymerization accelerator, the Polymerization accelerator comprising hexamethylenetetramine (HMTA).

10. The composition of claim 9, wherein said butylated hydroxyanisole is about 10,000 ppm, and wherein said sulfur dioxide is about 150 ppm.

11. A system for treating living tissue comprising:
an applicator comprising:
  a first reservoir disposed in a non-contact relationship with a second reservoir, wherein the first reservoir comprises:
    between about 83 weight % and about 89 weight % of a 2 octyl cyanoacrylate monomer;
    between about 3 weight % and about 5 weight % of a first viscosity modifier comprising polymethyl methacrylate (PMMA), wherein the first viscosity modifier comprises a molecular weight from about 400,000 Da to about 500,000 Da;
    between about 3 weight % and about 5 weight % of a second viscosity modifier comprising the PMMA, wherein the second viscosity modifier comprises the molecular weight from about 100,000 Da to about 130,000 Da;
    between about 3 weight % and about 6 weight % of tributyl 0-acetylcitrate (TBOAC);
    between about 3 weight % and about 7 weight % of acetone;
    between about 5000 parts per million (ppm) and about 15000 ppm of butylated hydroxyanisole; and
    between about 100 ppm and about 300 ppm of sulfur dioxide, and
  the second reservoir comprising:
    a polymerization initiator, wherein the polymerization initiator comprises benzalkonium chloride (BZC) having a weight % between about 0.1% to about 0.3%; and
    a polymerization accelerator, wherein the polymerization initiator comprises hexamethylenetetramine (HMTA) having the weight % between about 0.1% to about 0.3%; and
  an applicator tip capable of combining contents of the first reservoir with contents of the second reservoir to form an adhesive composition and then applying said adhesive composition to a living tissue.

12. A composition comprising:
about 88.35% by weight of 2-octyl cyanoacrylate having a purity of more than about 99% by weight;
from about 100 parts per million (ppm) to about 300 ppm of sulfur dioxide ($SO_2$) as a first polymerization inhibitor;
about 7337 ppm of butylated hydroxyanisole (BHA) as a second polymerization inhibitor;
about 5.06% by weight of a biocompatible plasticizer comprising tributyl O-acetylcitrate (TBOAC);
about 3.27% by weight of a viscosity modifier comprising polymethyl methacrylate (PMMA);
about 2.59% by weight of acetone; and
about 11.44% by weight of cured cyanoacrylate measured using HNMR at 50 degrees C. at 78 days after exposure to 10 kGy of electron beam radiation.

13. The composition of claim 12, said composition having an initial viscosity, wherein said initial viscosity increases less than about 10% after 90 days at 30 degrees C.

14. The composition of claim 13, wherein said initial viscosity increases less than about 10% after exposure to the 10 kGy of electron beam radiation.

15. The composition of claim 12, wherein said 2-octyl cyanoacrylate has a cured weight % of less than about 5% after 60 days at 30 degrees C.

16. The composition of claim 12, wherein said 2-octyl cyanoacrylate has a cured weight % of less than about 5% after 60 days at 50 degrees C.

17. A stable biocompatible wound closure adhesive composition comprising:
from about 83 percent to about 89 percent by weight of 2-octyl cyanoacrylate having a purity of more than about 99% by weight;
from about 100 parts per million (ppm) to about 300 ppm of sulfur dioxide ($SO_2$) as a first polymerization inhibitor;
from about 5000 ppm to 15000 ppm of butylated hydroxyanisole (BHA) as a second polymerization inhibitor;
from about 4 percent to about 6 percent by weight of a biocompatible plasticizer comprising tributyl O-acetylcitrate (TBOAC);
from about 3 percent to about 5 percent by weight of a first viscosity modifier comprising polymethyl methacrylate (PMMA), wherein the first viscosity modifier comprises a molecular weight from about 400,000 Da to about 500,000 Da;
from about 3 percent to about 5 percent by weight of a second viscosity modifier comprising the PMMA, wherein the second viscosity modifier comprises the molecular weight from about 100,000 Da to about 130,000 Da; and
from about 4 percent to about 6 percent by weight of acetone,
  wherein a setting time of the stable biocompatible wound closure adhesive composition is between about 60 and about 120 seconds,
  wherein a butt joint strength of the stable biocompatible wound closure adhesive composition is between about 5 and about 15 lbf, and
  wherein a peak reaction temperature of the stable biocompatible wound closure adhesive composition is less than about 40 degrees C.

18. The composition of claim 17,
wherein the stable biocompatible wound closure adhesive composition has an initial viscosity, and
wherein said initial viscosity increases less than about 10% after 90 days at 30 degrees C.

19. The composition of claim 18, wherein said initial viscosity increases less than about 10% after exposure to 10 kGy of electron beam radiation.

20. The composition of claim 17, wherein said 2-octyl cyanoacrylate has a cured weight % of less than about 5% after 60 days at 30 degrees C.

21. The composition of claim 17, wherein said 2-octyl cyanoacrylate has a cured weight % of less than about 5% after 60 days at 50 degrees C.

* * * * *